US007871811B2

United States Patent
Fang et al.

(10) Patent No.: US 7,871,811 B2
(45) Date of Patent: Jan. 18, 2011

(54) METHOD FOR ELIMINATING CROSSTALK BETWEEN WAVEGUIDE GRATING-BASED BIOSENSORS LOCATED IN A MICROPLATE AND THE RESULTING MICROPLATE

(75) Inventors: Ye Fang, Painted Post, NY (US); Ann M. Ferrie, Painted Post, NY (US); Norman H. Fontaine, Painted Post, NY (US); Anthony G. Frutos, Painted Post, NY (US); Eric J. Mozdy, Elmira, NY (US); Chuan-Che Wang, Ithaca, NY (US); Po Ki Yuen, Corning, NY (US)

(73) Assignee: Corning Incorporated, Corning, NY (US)

( * ) Notice: Subject to any disclaimer, the term of this patent is extended or adjusted under 35 U.S.C. 154(b) by 1386 days.

(21) Appl. No.: 11/101,096

(22) Filed: Apr. 7, 2005

(65) Prior Publication Data

US 2006/0229818 A1    Oct. 12, 2006

(51) Int. Cl.
  *C12M 1/00*  (2006.01)
  *C12Q 1/68*  (2006.01)
  *G01N 1/00*  (2006.01)
(52) U.S. Cl. ................ 435/283.1; 435/6; 422/50
(58) Field of Classification Search .............. None
  See application file for complete search history.

(56) References Cited

U.S. PATENT DOCUMENTS

| | | | |
|---|---|---|---|
| 4,815,843 A | 3/1989 | Tiefenthaler et al. | 356/128 |
| 6,592,784 B2 | 7/2003 | Hasegawa et al. | 252/587 |
| 6,818,886 B2 | 11/2004 | Tiefenthaler | 250/282 |
| 2002/0004204 A1* | 1/2002 | O'Keefe | 435/6 |
| 2002/0127565 A1 | 9/2002 | Cunningham et al. | 435/6 |
| 2002/0168295 A1 | 11/2002 | Cunningham et al. | 422/82.05 |
| 2003/0017580 A1 | 1/2003 | Cunningham et al. | 435/287.2 |
| 2003/0017581 A1 | 1/2003 | Li et al. | 435/287.2 |
| 2003/0026891 A1 | 2/2003 | Qiu et al. | 427/58 |
| 2003/0027327 A1 | 2/2003 | Cunningham et al. | 435/287.2 |
| 2003/0027328 A1 | 2/2003 | Cunningham et al. | 435/287.2 |
| 2003/0032039 A1 | 2/2003 | Cunningham et al. | 435/6 |
| 2003/0059855 A1 | 3/2003 | Cunningham et al. | 435/7.9 |

(Continued)

OTHER PUBLICATIONS

Kastberger et al. Infrared imaging technology and biological applications. Behavior Research Methods, Instruments, & Computers. 2003, vol. 35, pp. 429-439.*

(Continued)

*Primary Examiner*—Russell S Negin
(74) *Attorney, Agent, or Firm*—Gregory B. Butler; Thomas R. Beall

(57) ABSTRACT

The present invention includes several methods for modifying the current processes of manufacturing optical sensing microplates that use continuous waveguide films to reduce/eliminate crosstalk between the biosensors that are incorporated within wells. The methods include (1) physically deteriorating/removing the waveguide film between individual biosensors; (2) chemically depositing highly absorbing materials within the waveguide film between individual biosensors; (3) patterning disordered (scattering) regions between the diffraction gratings that define individual biosensors; (4) using a specific mask and depositing individual patches of waveguide film, where each patch defines at least one biosensor. Each of these methods and several other methods described herein prevent the propagation of light between individual sensing regions, thereby eliminating optical crosstalk between the biosensors. The present invention also includes the resulting microplate.

31 Claims, 9 Drawing Sheets

U.S. PATENT DOCUMENTS

| | | | |
|---|---|---|---|
| 2003/0068657 A1 | 4/2003 | Lin et al. | 435/7.9 |
| 2003/0077660 A1 | 4/2003 | Pien et al. | 435/7.1 |
| 2003/0092075 A1 | 5/2003 | Pepper | 435/7.9 |
| 2003/0113766 A1 | 6/2003 | Pepper et al. | 435/6 |
| 2003/0124029 A1* | 7/2003 | Webb et al. | 422/102 |
| 2004/0014102 A1* | 1/2004 | Chen et al. | 435/6 |
| 2004/0132172 A1 | 7/2004 | Cunningham et al. | 435/287.2 |
| 2004/0132214 A1 | 7/2004 | Lin et al. | 436/518 |
| 2004/0151626 A1 | 8/2004 | Cunningham et al. | 422/58 |
| 2004/0223881 A1 | 11/2004 | Cunningham et al. | 422/82.05 |
| 2005/0064427 A1* | 3/2005 | Gluch et al. | 435/6 |

OTHER PUBLICATIONS

Sundaram et al. 2-Color QWIP FPAs. Proceedings of the SPIE, vol. 4028, 2000, pp. 311-317.*

Definition of "photoresist." HCC Industries 2007; obtained online on Mar. 2, 2010 << http://hccindustries.com/products/technical-information/definition-of-terms/default.asp >> 5 pages.*

Jordan et al., "Surface Plasmon Resonance Imaging Measurements of Electrostatic Biopolymer Adsorption onto Chemically Modified Gold Surfaces", Anal. Chem., 1997, vol. 69, pp. 1449-1456.

Morhard et al., "Immobilization of Antibodies in Micropatterns for Cell Detection by Optical Diffraction", Sensors and Actuators B, 2000, vol. 70, pp. 232-242.

Jin et al., "A Biosensor Concept Based on Imaging Ellipsometry for Visualization of Biomolecular Interactions", Analytical Biochemistry, 1995, vol. 232, pp. 69-72.

Brecht et al., "Optical Probes and Transducers", Biosensors and Bioelectronics, 1995, vol. 10, pp. 923-936.

Huber et al., "Direct Optical Immunosensing (Sensitivity and Selectivity)", Sensors and Actuators B, 1992, vol. 6, pp. 122-126.

Tiefenthaler et al., "Sensitivity of Grating Couplers as Integrated Optical Chemical Sensors", J. Opt. Soc. Am. B, 1989, vol. 6, pp. 209-220.

* cited by examiner

METHOD FOR ELIMINATING CROSSTALK BETWEEN WAVEGUIDE GRATING-BASED BIOSENSORS LOCATED IN A MICROPLATE AND THE RESULTING MICROPLATE

BACKGROUND OF THE INVENTION

1. Field of the Invention

The present invention relates to a method for reducing/eliminating crosstalk between waveguide grating-based biosensors that are located within the wells of a microplate and the resulting microplate.

2. Description of Related Art

Manufacturers of optical sensing microplates (OSMs) have been trying to develop new methods they can use to manufacture a microplate so as to eliminate crosstalk between waveguide grating-based biosensors that are incorporated within the wells of the microplate. Several new methods for eliminating crosstalk between biosensors incorporated within the wells of a microplate are the subject of the present invention.

BRIEF DESCRIPTION OF THE INVENTION

The present invention includes several methods for modifying the current processes of manufacturing optical sensing microplates that use continuous waveguide films to eliminate crosstalk between the biosensors that are incorporated within wells. The methods include (1) physically deteriorating/removing the waveguide film between individual biosensors; (2) chemically depositing highly absorbing materials onto the waveguide film between individual biosensors; (3) patterning disordered (scattering) regions between the diffraction gratings that define individual biosensors; (4) using a specific mask and depositing individual patches of waveguide film, where each patch defines at least one biosensor. Each of these methods and several other methods described herein prevent or significantly reduce the propagation of light between individual sensing regions, thereby eliminating or reducing optical crosstalk between the biosensors. The present invention also includes the resulting microplate.

BRIEF DESCRIPTION OF THE DRAWINGS

A more complete understanding of the present invention may be had by reference to the following detailed description when taken in conjunction with the accompanying drawings wherein.

DETAILED DESCRIPTION OF THE DRAWINGS

A method for eliminating crosstalk between waveguide grating-based biosensors which are incorporated within the wells of a microplate is described herein. However, prior to describing this method and several different embodiments of this method a brief discussion is provided about the structure and function of waveguide grating-based biosensors. Also, provided is a brief description about several traditional methods which are used today in an attempt to address the problematical crosstalk that occurs between biosensors when they are incorporated within the wells of a microplate.

Figure 1:
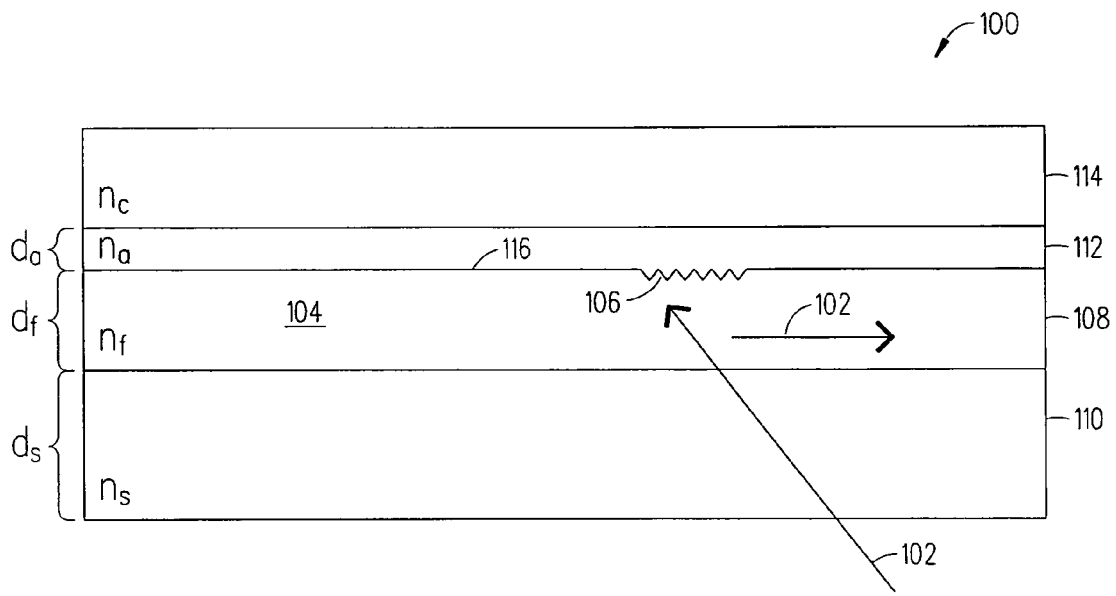
FIG. 1 (PRIOR ART) is a diagram illustrating a classical four layer waveguide grating-based biosensor.

FIG. 1 (PRIOR ART) is a side view of a waveguide grating-based biosensor 100 which is an evanescent-wave sensor that is based on the resonant coupling of light 102 into a waveguide 104 by means of a diffraction grating 106. As shown, the classical four layer waveguide grating-based biosensor 100 includes a thin waveguide film 108 of a high refractive index material (e.g., $n_f \sim 2.36$ for $Nb_2O_5$) with a thickness of $d_f$. The waveguide film 108 is located on a substrate 110 of lower index material (e.g., $n_s \sim 1.50$ for Corning's 1737 glass) with a thickness of $d_s$. Immobilized on the waveguide film 108 is a layer of probe molecules (e.g., biologicals such as proteins or DNA, chemicals such as synthetic ligands, or biochemicals such as synthetic peptides or engineered oligonucleotides) 112 with a refractive index ($n_a$) of around 1.4 and a thickness of $d_a$. And, on top of the layer of probe molecules (e.g., biologicals) 112 is a cover medium 114 which is a biological solution with a refractive index ($n_c$) of around 1.35.

A laser or luminescent diode (not shown) emits light 102 that is coupled into the waveguide 104 only at a specific angle and wavelength. The coupling angle and wavelength are determined by a phase-matching condition of the waveguide-grating structure which occurs when a non-normal component of a propagation vector of the incoming light 102, a wavevector of the diffraction grating 106, and a propagation constant of a guided mode ($\beta$) all sum to zero. At these specific angles/wavelengths, the coupled light 102 propagates parallel to a surface 116 in the plane of the waveguide film 108 creating an electromagnetic field in the biological layer 112/cover medium 114. The guided waves or modes of the coupled light 102 in the planar waveguide 104 are $TE_m$ (transverse electric or s-polarized) or $TM_m$ (transverse magnetic or p-polarized), where m=0, 1, 2, . . . is the mode number. A given mode of the coupled light 102 propagates as a guided wave only if two conditions are met: (a) the refractive index of the waveguide film 108 is larger than the refractive indices of the substrate 110 and probe molecule (e.g., biological) layer 112/cover medium 114; and (2) the thickness $d_f$ of the waveguide film 108 is larger than a value well known in the field as the cut-off thickness (not shown).

Because the evanescent field of the guided mode projects into the probe (e.g., biological) layer 112/cover liquid 114, the waveguide mode is extremely sensitive to the cover environment. When a biological binding event occurs at or near the waveguide surface 116, the effective index of the probe molecule layer 112/cover medium 114 changes in accordance with the mass of the biological moieties bound. When the effective index of the cover layer changes, the waveguide propagation constant of the waveguide mode also changes in accordance with Maxwell's electromagnetic equations. This means that the preferred input light coupling angle/wavelength condition will also change in accordance with the change of the waveguide propagation constant. It is this macroscopic physical change that is monitored so as to indicate the microscopic biological binding event.

For a more detailed discussion about the structure and function of the waveguide grating-based biosensor 100 reference is made to the following documents:

U.S. Pat. No. 4,815,843 entitled "Optical Sensor for Selective Detection of Substances and/or for the Detection of Refractive Index Changes in Gaseous, Liquid, Solid and Porous Samples".

Jordan & Corn, "Surface Plasmon Resonance Imaging Measurements of Electrostatic Biopolymer Adsorption onto Chemically Modified Gold Surfaces," Anal. Chem., 1997, 69:1449-1456.

Morhard et al., "Immobilization of antibodies in micropatterns for cell detection by optical diffraction," Sensors and Actuators B, 2000, 70, 232-242.

Jin et al., "A biosensor concept based on imaging ellipsometry for visualization of biomolecular interactions," Analytical Biochemistry, 1995, 232, 69-72.

Huber et al., "Direct optical immunosensing (sensitivity and selectivity)," Sensors and Actuators B, 1992, 6, 122-126.

Brecht & Gauglitz, "Optical probes and transducers," Biosensors and Bioelectronics, 1995, 10, 923-936.

Tiefenthaler et al., "Sensitivity of grating couplers as integrated optical chemical sensors" J. Opt. Soc. Am. B, 1989, 6, 209-220.

The contents of these documents are hereby incorporated by reference herein.

Figure 2:
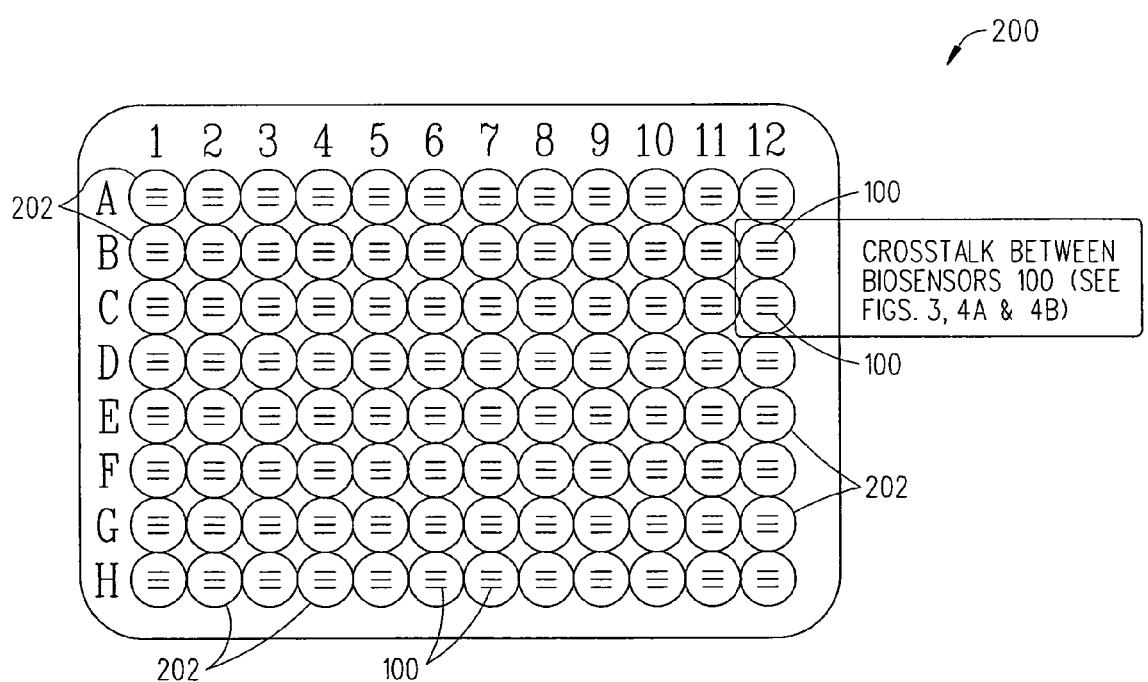
FIG. 2 (PRIOR ART) is a top view of a traditional optical sensing microplate.

Single waveguide grating-based biosensors 100 are commonly used for affinity determination, where probe molecules are immobilized or tethered on the waveguide surface 116 and used as a recognition sites to "fish" out a specific binding target from a sample in the cell medium 114, or to determine the binding affinity with a compound or ligand in the medium 114. With the changing paradigm in the drug discovery space, the number of drug targets is expanding and so is the volume of assay points performed in high-throughput screens. To take advantage of the fluorescent label-free detection capability of the waveguide grating-based biosensor 100 and to meet the industrial demand for high-throughput screens, a microplate which has a two-dimensional (2-D) array of the biosensors 100 located on the bottoms of its wells has been proposed. FIG. 2 (PRIOR ART) is a top view showing an example of such an optical sensing microplate (OSM) 200.

Figure 3:
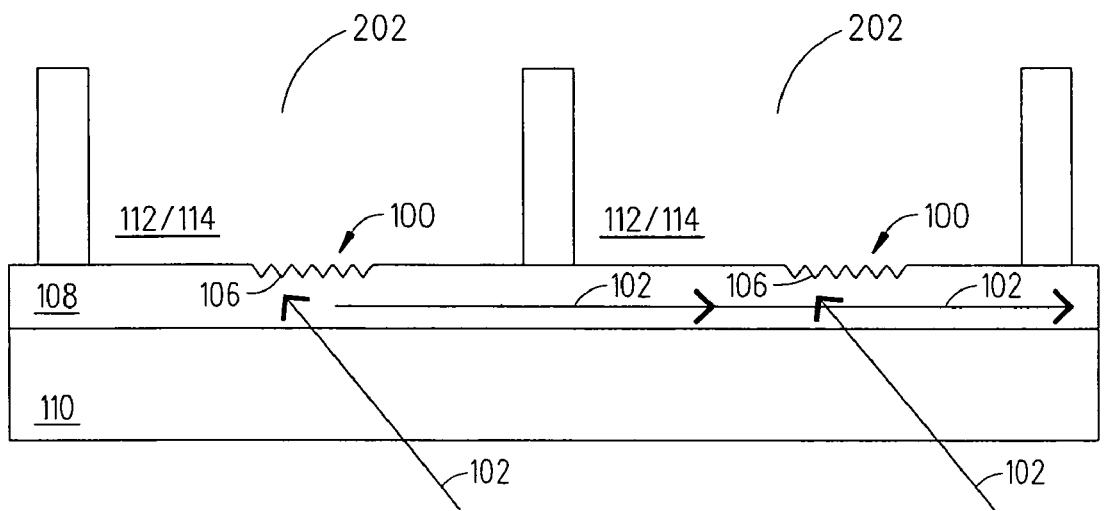
FIG. 3 (PRIOR ART) is a cross-sectional side view of two wells and two biosensors from the traditional microplate shown on FIG. 2.

The current method of manufacturing the microplate 200 involves vapor deposition of a continuous waveguide film 108 onto a support substrate 110 (e.g., glass 110) presenting grating structured areas 106 (see FIG. 3). The grating structured areas 106 can be formed on the support substrate 110 using an embossing method when the support substrate 110 has a pre-coated polymer layer (not shown). Or, the grating structured areas 106 can be formed directly on the support substrate 110 using a chemical or lithographic etching method (typically by employing a photoresist process). Another method is to laminate a continuous waveguide film 108 with grating structured areas 106 already formed therein on the support substrate 110 (see FIGS. 1 and 3). In each case, because of the nature of the continuous waveguide film 108, there is crosstalk between wells 202 as shown in FIG. 3 (PRIOR ART).

FIG. 3 (PRIOR ART) is a side view of two nearby wells 202 in the 96-well microplate 200. This figure highlights the underlying structure of a conventional waveguide grating-based biosensor 100: a waveguide film 108 made from a high refractive index (e.g., $n_F \sim 2.36$ for $Nb_2O_5$) material bordered by lower index layers, namely a substrate 110 (e.g., $n_s \sim 1.50$ for Corning 1737 glass) and a biological layer 112/cover medium 114.

Because a continuous waveguide film 108 having separated grating structures 106 formed therein is used in the microplate 200, there can be significant crosstalk between nearby wells 202 that are located in the same column or row. And, due to the nature of the incident light and the coupling to the mode, the cross-talk that is induced by the coupled mode crossing from one sensor 100 to another sensor 100 may be unidirectional. Hence the cross-talk may occur from one well 202 to an adjacent well 202, but not in reverse. However, cross-talk may occur in both directions simultaneously if the nature of the illumination and the waveguide modes defined by the structure are such as to create excitation of more than one mode and/or those modes propagate in opposite directions. In this case, cross-talk between wells 202 may be bi-directional in that responses from two adjacent wells 202 may mutually influence each other. Another possible mechanism for the occurrence of the crosstalk is due to the trapping and propagation of scattered light in the continuous waveguide film; this may result from the many possible reflections in the multi-layer structure in conjunction with the waveguiding ability of the high index film.

Figure 4A:
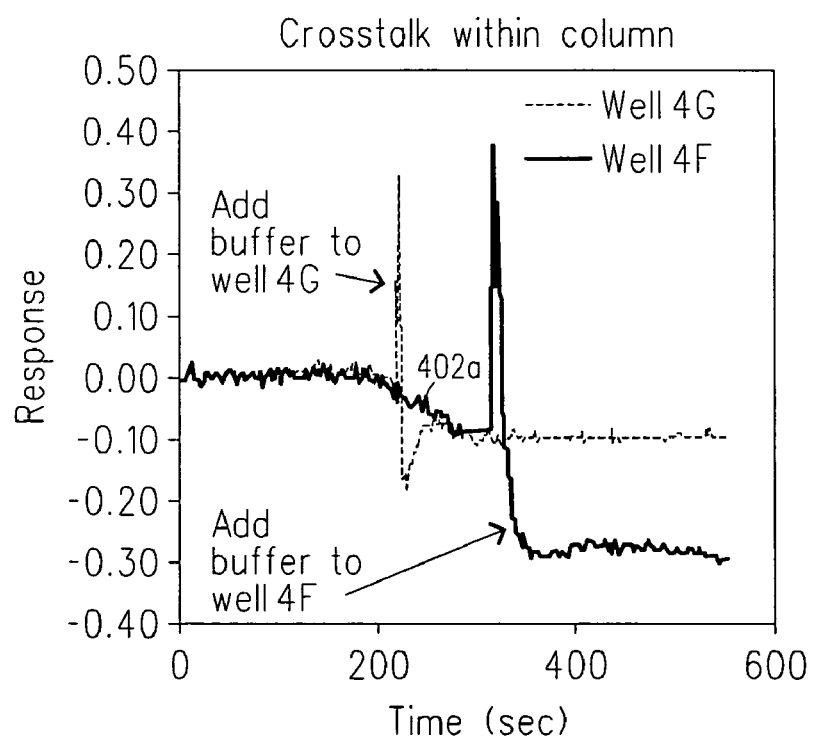
FIGS. 4A and 4B (PRIOR ART) are two graphs that demonstrate the crosstalk that occurs between the biosensors that are located in wells of the traditional microplate shown in FIG. 2.
Figure 4B:
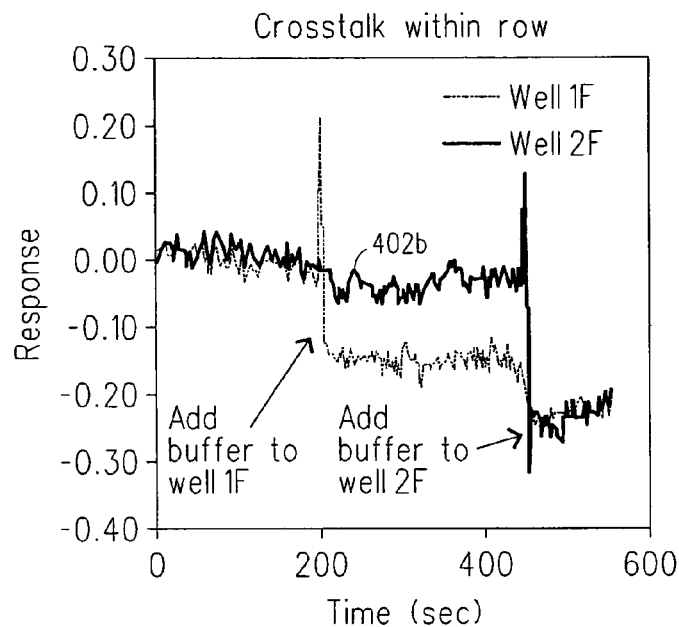

Two experimental examples of crosstalk between nearby wells are shown in FIGS. 4A and 4B. For two nearby wells 4F and 4G located in the same column, there exists a crosstalk signal 402a which can be seen in FIG. 4A. The crosstalk signal 402a was detected in well 4F when a buffer solution was added into well 4G (FIG. 4A). Similarly, for two nearby wells 1F and 2F located in the same row, there also exists a crosstalk signal 402b which can seen in FIG. 4B. The crosstalk signal 402b was detected in the well 2F when a buffer solution was added into the well 1F (FIG. 4B). The crosstalk within nearby wells 1F and 2F (for example) is due to the light 102 propagating within the continuous waveguide film 108. It should be readily appreciated that this crosstalk problem can exist regardless of the grating structure's 106 location relative to the waveguide film 108 (e.g. above or below).

In the past, the problem of crosstalk in microplates could be avoided by interrogating only a few biosensors 100 at one time. For example, the optical interrogation system (not shown) might only interrogate one biosensor 100 at a time. Or, the optical interrogation system might interrogate every other biosensor 100, so as to avoid nearest-neighbor (the most significant) crosstalk. Since the waveguide grating-based biosensors 100 used today typically utilize one-dimensional propagation, the crosstalk can also be much stronger for neighboring wells 202 which are located parallel to the direction of propagation. In such cases, other optical interrogation systems have been designed to simultaneously interrogate neighboring wells 202 only in a direction perpendicular to the propagation direction (e.g. only one row or one column at a time). Unfortunately, all of these approaches necessitate that only a subset of the biosensors 100 in the microplate 200 can be interrogated at a given time. This increases the overall time required to interrogate the entire microplate 200, and undermines the inherent multiplexing capability of the full microplate 200. The microplate 500 and method 600 of the present invention remove this crosstalk barrier which allows the parallel interrogation of all of the biosensors 100 located in the microplate 500.

Figure 5:
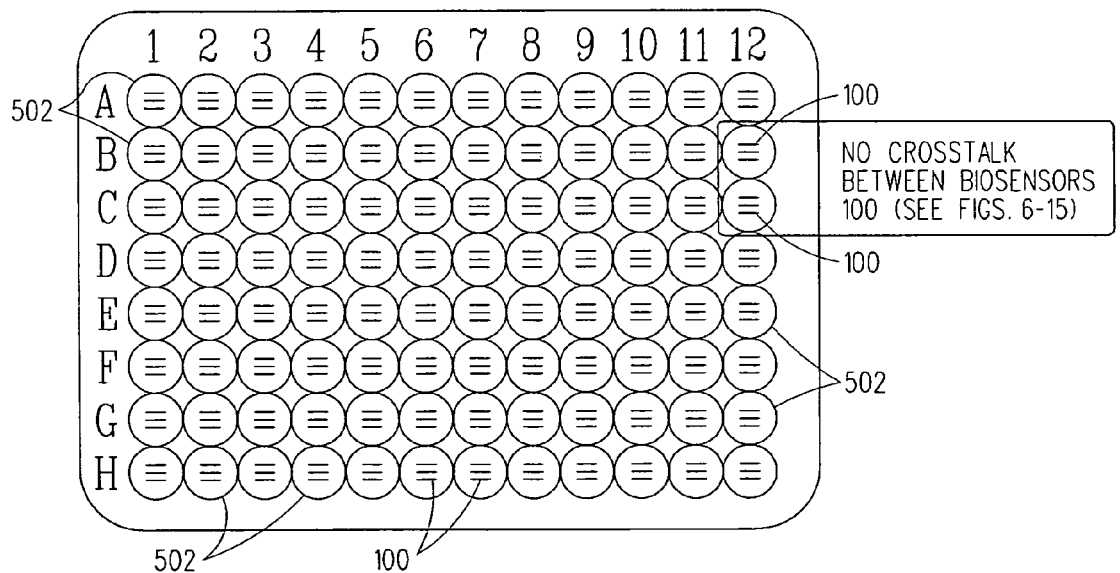
FIG. 5 is a top view of an optical sensing microplate in accordance with the present invention.
Figure 6:
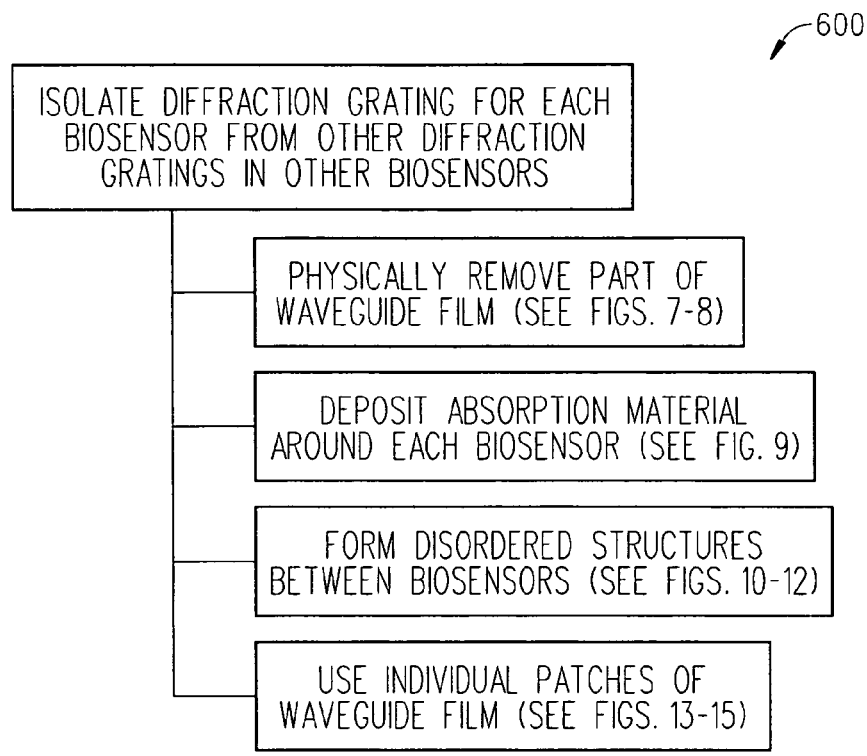
FIG. 6 is a flowchart illustrating the basic steps of a method for eliminating crosstalk between biosensors that are located within the wells of an optical sensing microplate in accordance with the present invention.

FIGS. 5 and 6 respectively illustrate a top view of an exemplary 96-well microplate 500 and a flowchart of a method 600 for eliminating crosstalk between biosensors 100 located in the wells 502 of the microplate 500 in accordance with the present invention. The method 600 eliminates crosstalk between biosensors 100 located within the wells 502 of the microplate 500 by isolating the waveguide 104 associated with each biosensor 100 from other waveguides 104 associated with other biosensors 100. Several different embodiments of method 600 are described in detail below with respect to FIGS. 7-15.

Figure 7:
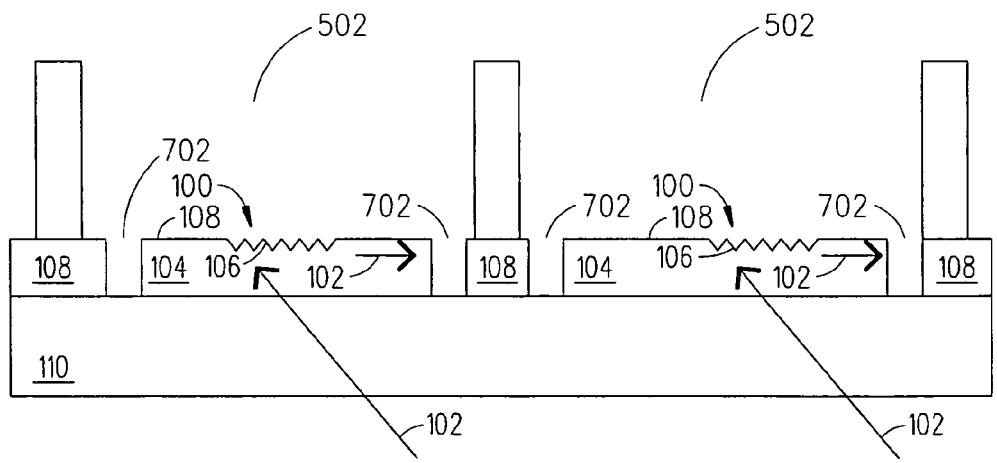
FIG. 7 is a cross-sectional side view of two nearby wells in the microplate shown in FIG. 5 where the two biosensors located in the bottom of the two wells have been isolated from one another so as to prevent crosstalk between those biosensors in accordance with a first embodiment of the present invention.
Figure 8A:
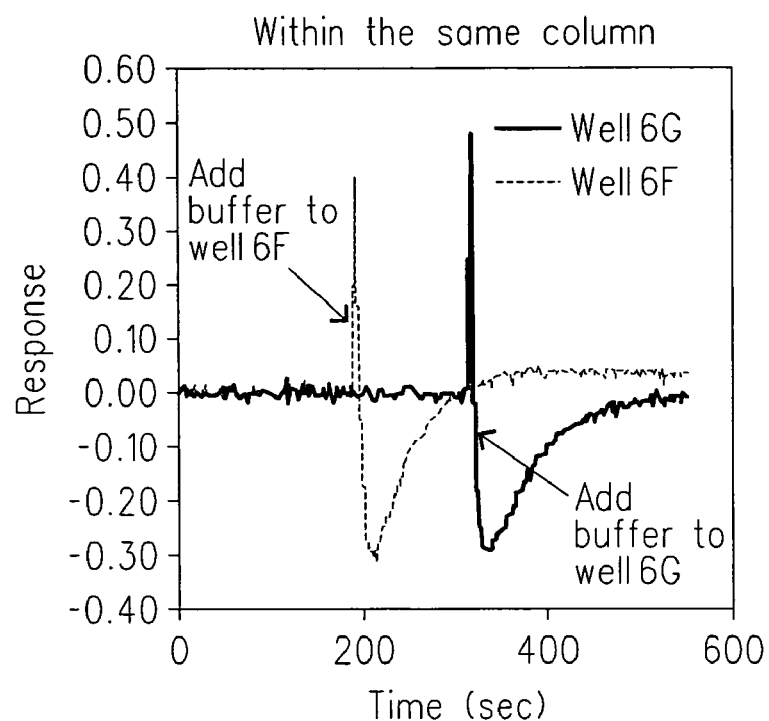
FIGS. 8A and 8B are two graphs generated from an experiment that demonstrates there is no crosstalk between the biosensors which were isolated from one another in accordance with the first embodiment of the present invention.
Figure 8B:
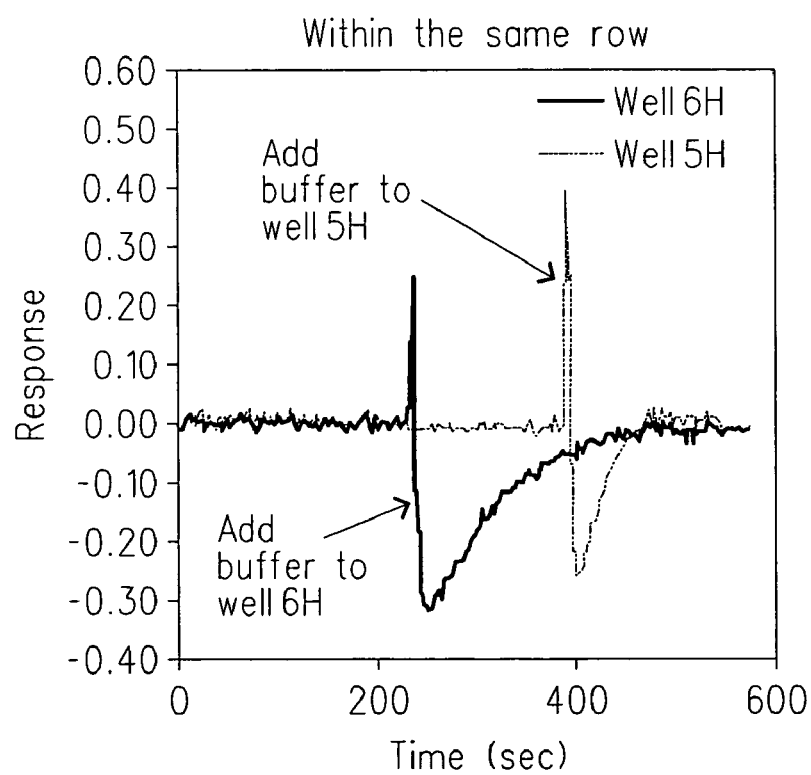

FIG. 7 shows the side view of two nearby wells 502 in the 96-well microplate 500 where the two biosensors 100 located in the bottom of the two wells 502 have been isolated from one another so as to prevent crosstalk between those biosensors 100 in accordance with a first embodiment of the present invention. In this embodiment, each diffraction grating 106/waveguide 104 is isolated from other diffraction gratings 106/waveguides 104 by physically removing/deteriorating a portion 702 of the waveguide film 108 that is preferably located around the perimeter of each diffraction grating 106/waveguide 104. In this example, the diffraction gratings 106 are shown formed within the waveguide film 108. The physical removal/deterioration of a portion 702 of the waveguide film 108 between the sensing areas associated with the diffraction grating 106/waveguide 104 prevents light 102 from propagating between biosensors 100 (compare to FIG. 3). One method that can be used to physically remove or physically deteriorate the waveguide film 108 between the grating structures 106 includes scratching the waveguide film 108. Because a portion 702 of the waveguide film 108 is removed from around each of the grating structures 106 formed therein, there is no crosstalk between biosensors 100 that are in the same column or same row when a buffer solution is added in one of the wells 502. Experimental data to illustrate this is shown in FIGS. 8A and 8B.

Figure 9:
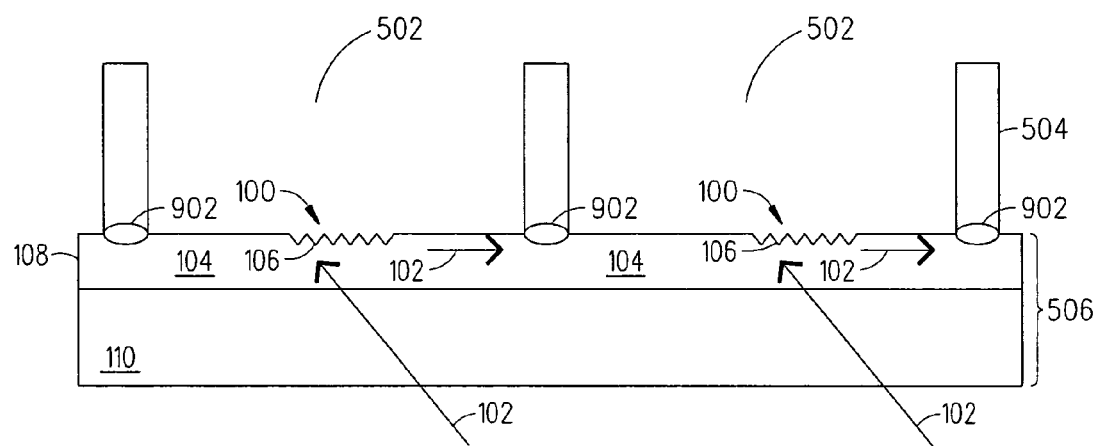
FIG. 9 is a cross-sectional side view of two nearby wells in the microplate shown in FIG. 5 where the two biosensors located in the bottom of the two wells have been isolated from one another so as to prevent crosstalk between those biosensors in accordance with a second embodiment of the present invention.

FIG. 9 shows the side view of two nearby wells 502 in the 96-well microplate 500 where the two biosensors 100 located in the bottom of the two wells 502 have been isolated from one another so as to prevent crosstalk between those biosensors 100 in accordance with a second embodiment of the present invention. In this embodiment, each diffraction grating 106/waveguide 104 is isolated from other diffraction gratings 106/waveguides 104 by depositing an absorption material 902 within or upon a portion of the waveguide film 108 that is preferably located around the perimeter of each diffraction grating 106. In this example, the diffraction gratings 106 are shown formed in the waveguide film 108. The absorption material 902 is deposited between the sensing areas associated with the diffraction gratings 106/waveguides 104 so that it can absorb crosstalk-producing light 102. In one embodiment, the absorbing material 902 can be deposited in the contact area between the holey plate 504 and the bottom insert plate 506 by any state-of-the-art adhesive or heat bonding method. Alternatively, the absorbing material 902 can be chemically deposited and attached in the area where the side wall and bottom surface meet in each well 502. In the preferred embodiment, the optically-absorbing material 902 can be a metal (e.g. silver) film vapor-deposited for attenuation of near infrared light. Or, the optically-absorbing material 902 can be a polymer containing a near infrared-absorbing dye (e.g., sulfonic acid group-containing polymers).

Figure 10:
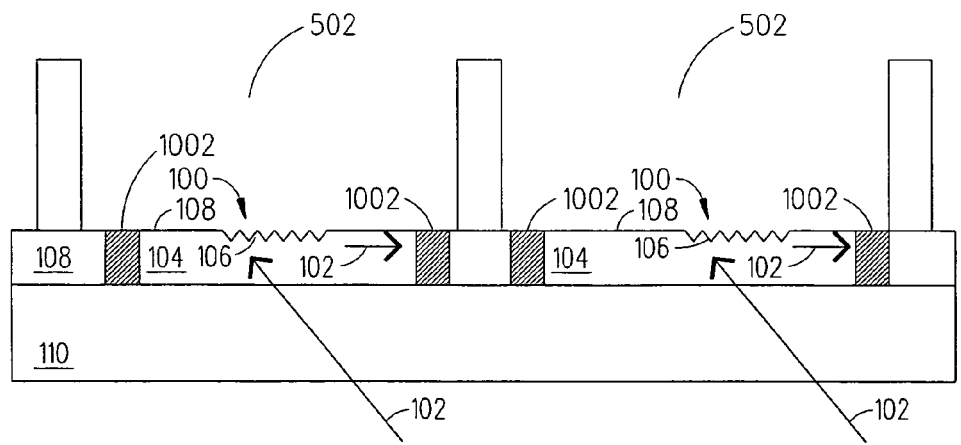
FIG. 10 is a cross-sectional side view of two nearby wells in the microplate shown in FIG. 5 where the two biosensors located in the bottom of the two wells have been isolated from one another so as to prevent crosstalk between those biosensors in accordance with a third embodiment of the present invention.

FIG. 10 shows the side view of two nearby wells 502 in the 96-well microplate 500 where the two biosensors 100 located in the bottom of the two wells 502 have been isolated from one another so as to prevent crosstalk between those biosensors 100 in accordance with a third embodiment of the present invention. In this embodiment, each diffraction grating 106/waveguide 104 is isolated from other diffraction gratings 106/waveguides 104 by using a mask and lithography (or other embossing/etching processes) to pattern disordered structures 1002 within a portion of the waveguide film 108 that is preferably located around the perimeter of each diffraction grating 106/waveguide 104. In this example, the diffraction gratings 106 are shown formed within the waveguide film 108. As can be seen, the disordered structures 1002 between the diffraction gratings 106/waveguides 104 scatter the potential crosstalk light 102 out of the waveguide 104 before the light 102 reaches a neighboring biosensor 100. Fabrication of the disordered structures 1002 can take place when the diffraction gratings 106 are being formed within the waveguide film 108.

Figure 11:
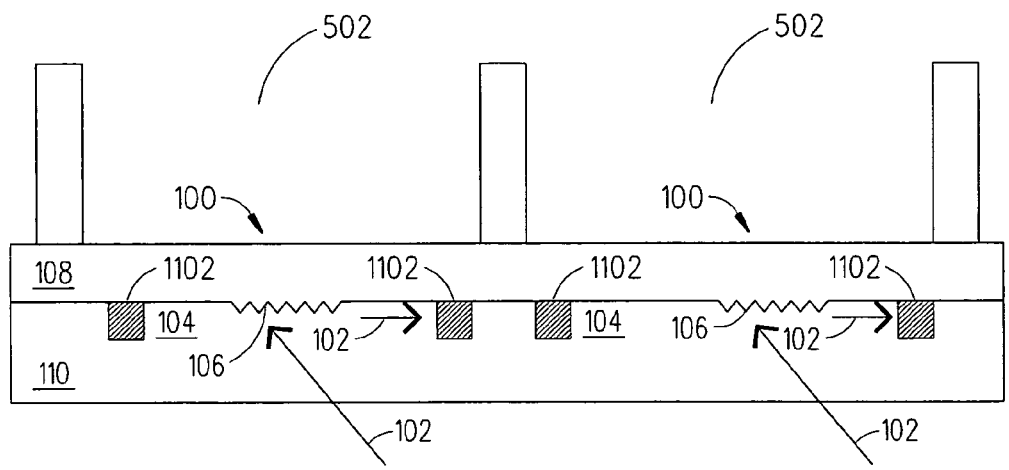
FIG. 11 is a cross-sectional side view of two nearby wells in the microplate shown in FIG. 5 where the two biosensors located in the bottom of the two wells have been isolated from one another so as to prevent crosstalk between those biosensors in accordance with a fourth embodiment of the present invention.
Figure 12:
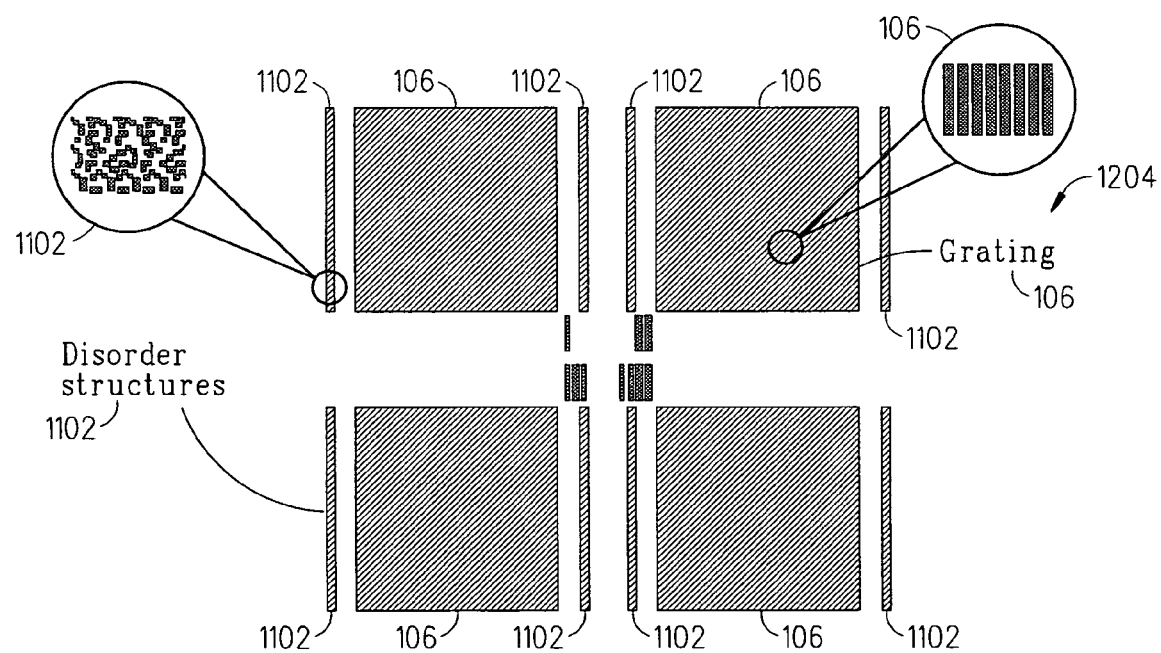
FIG. 12 is a diagram of an exemplary lithographic mask that can be used to isolate the biosensors shown in FIG. 11.

FIG. 11 shows the side view of two nearby wells 502 in the 96-well microplate 500 where the two biosensors 100 located in the bottom of the two wells 502 have been isolated from one another so as to prevent crosstalk between those biosensors 100 in accordance with a fourth embodiment of the present invention. In this embodiment, each diffraction grating 106/waveguide 104 is isolated from other diffraction gratings 106/waveguides 104 by using a mask and lithography (or other etching/embossing process) to pattern disordered structures 1102 within a portion of the substrate 110 that is preferably located around the perimeter of each diffraction grating 106/waveguide 104. In this example, the diffraction gratings 106 are shown formed in the substrate 110. As can be seen, the disordered structures 1102 located between the diffraction gratings 106/waveguides 104 effectively scatter the potential crosstalk light 102 out of the waveguide 104 before it reaches a neighboring biosensor 100. Fabrication of the disordered structures 1102 can take place when the diffraction gratings 106 are being formed within the substrate 110. An exemplary lithographic mask 1204 that can be used to create a series of disordered structures 1102 between four diffraction gratings 106 is shown in FIG. 12. After the diffraction gratings 106 and disordered structures 1002 are formed in the substrate 110, then the waveguide film 108 is deposited over the entire substrate 110 via any of the aforementioned fabrication techniques.

Figure 13:
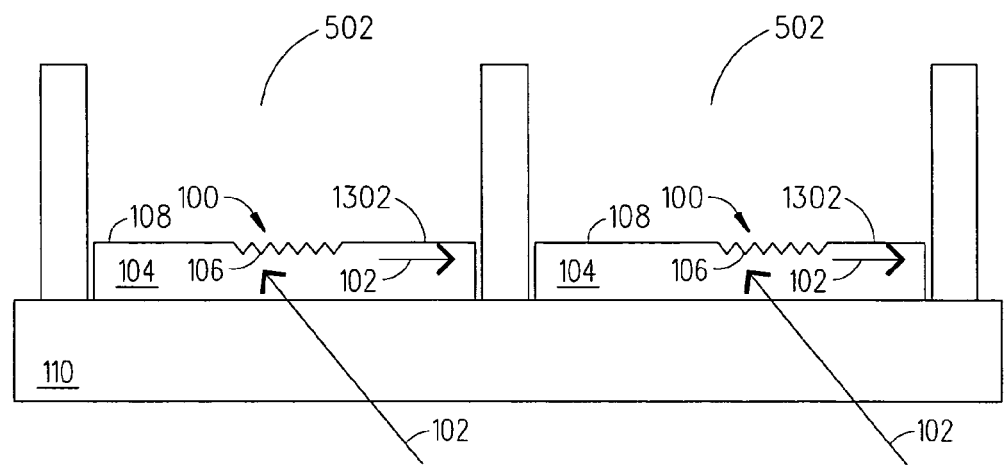
FIG. 13 is a cross-sectional side view of two nearby wells in the microplate shown in FIG. 5 where the two biosensors located in the bottom of the two wells have been isolated from one another so as to prevent crosstalk between those biosensors in accordance with a fifth embodiment of the present invention.

FIG. 13 shows the side view of two nearby wells 502 in the 96-well microplate 500 where the two biosensors 100 located in the bottom of the two wells 502 have been isolated from one another so as to prevent crosstalk between those biosensors 100 in accordance with a fifth embodiment of the present invention. In this embodiment, each diffraction grating 106/waveguide 104 is isolated from other diffraction gratings 106/waveguides 104 by using a mask and depositing individual patches of waveguide film 108 over the substrate 110. Each patch 1302 has one of the diffraction gratings 106 formed therein. Because of the lack of waveguide film 108 between sensing regions, the light 102 cannot propagate between neighboring biosensors 100 to produce crosstalk.

Figure 14:
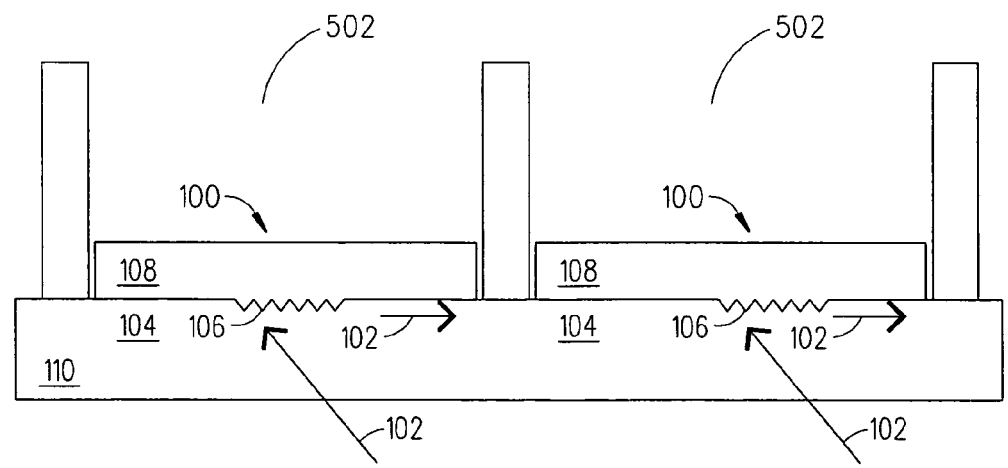
FIG. 14 is a cross-sectional side view of two nearby wells in the microplate shown in FIG. 5 where the two biosensors located in the bottom of the two wells have been isolated from one another so as to prevent crosstalk between those biosensors in accordance with a sixth embodiment of the present invention.
Figure 15:
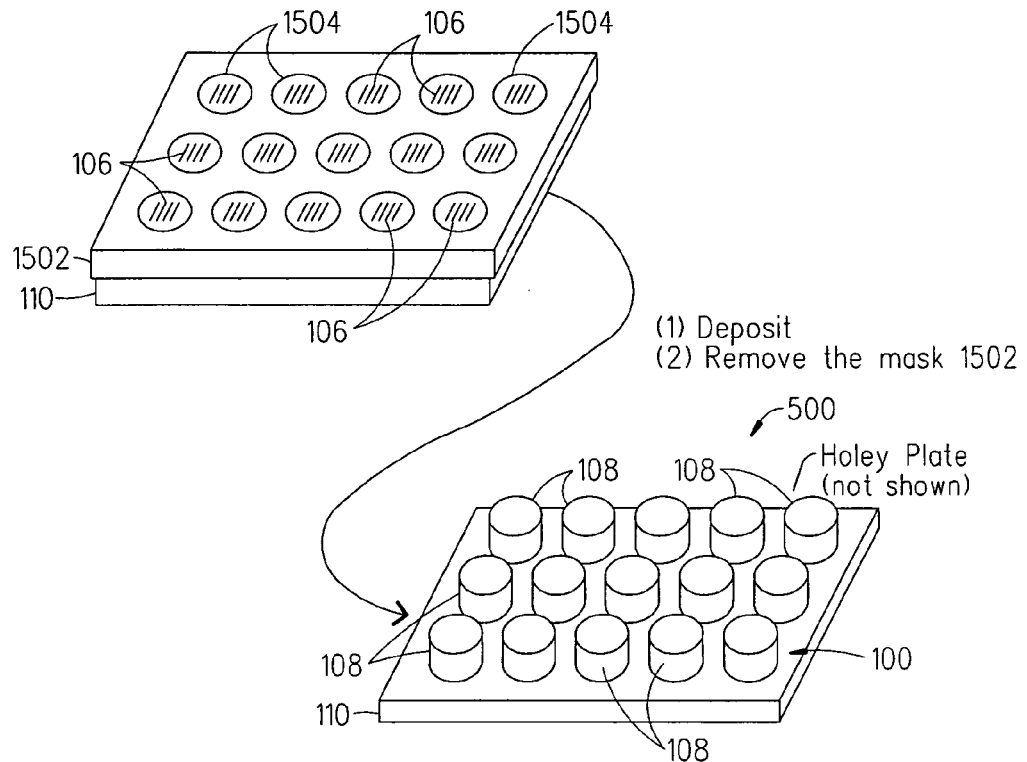
FIG. 15 is a diagram used to help explain the process that can be used to isolate the biosensors shown in FIG. 14.

FIG. 14 shows the side view of two nearby wells 502 in the 96-well microplate 500 where the two biosensors 100 located in the bottom of the two wells 502 have been isolated from one another so as to prevent crosstalk between those biosensors 100 in accordance with a sixth embodiment of the present invention. In this embodiment, each diffraction grating 106/waveguide 104 is isolated from other diffraction gratings 106/waveguides 104 by using a mask and depositing individual patches of waveguide film 108 over the diffraction gratings 106 that were previously formed in the substrate 110. FIG. 15 illustrates this process where the solid support substrate 110 (e.g., glass 100) having a given number of diffraction gratings 106 formed therein is positioned against a mask 1502 such that under each open area 1504 in the mask 1502 there is at least one diffraction grating 106. Then, an individual patch of waveguide film 108 (e.g., $Nb_2O_5$) is deposited within each open area 1504 on top of the substrate 110. The mask 1502 is removed, and a holey plate (not shown) with the identical given number of openings as was in the mask 1502 is attached to the solid support substrate 110 to form the microplate 500.

Some additional features and advantages of using the optical LID system 100 of the present invention are as follows:

It is well known that crosstalk between wells in optical sensing microplates that use a continuous waveguide film can pose issues or problems for data analysis and assay sensitivity and robustness. The methods described herein to eliminate this crosstalk and can significantly improve the quality of the microplates for affinity screening and functional cell assay-based screening.

The present invention by altering the waveguide sensor itself eliminates crosstalk between wells as opposed to simply avoiding crosstalk by interrogating non-neighbor sensors, as practiced in the prior art. This allows the entire microplate to be utilized simultaneously, which is critical for addressing the trend in industry towards using higher and higher throughput assays.

The present invention described herein includes several different methods for the design and manufacture of the biosensor, which gives one the flexibility and/or the possibility of using more than one of these methods at the same time in the case of particularly strong crosstalk.

Figure 16:
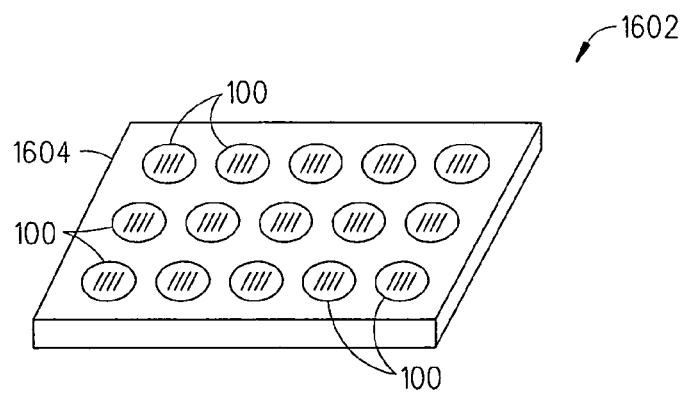
FIG. 16 is a perspective view of a slide made in accordance with the present invention.

It should be appreciated that the present invention can be applied to slides as well as microplates. Referring to FIG. 16, an exemplary slide 1602 is shown that has a base 1604 with an array of waveguide grating-based biosensors 100 (15 shown) that can be isolated from one another in accordance with anyone or any number of the techniques described herein which can be used to reduce/eliminate crosstalk between the waveguide grating-based biosensors 100.

It should be appreciated that the biosensor 100 described herein can be used along with different optical LID techniques to study a variety of biomolecular binding events that can occur on the surface of the biosensor 100 including (for example): oligonucleotides interactions, antibody-antigen interactions, hormone-receptor interactions, and enzyme-substrate interactions.

Although several embodiments of the present invention have been illustrated in the accompanying Drawings and described in the foregoing Detailed Description, it should be understood that the invention is not limited to the embodiments disclosed, but is capable of numerous rearrangements, modifications and substitutions without departing from the spirit of the invention as set forth and defined by the following claims.

What is claimed is:

1. A method for eliminating crosstalk of coupled light between a plurality of waveguide grating-based biosensors which are located in bottoms of a plurality of wells in a microplate, said method comprising the step of:

isolating a waveguide within each biosensor from other waveguides that are within other biosensors to eliminate the crosstalk of coupled light between each of the biosensors, wherein the waveguide within each biosensor has coupled light propagating therein, and wherein the plurality of biosensors are formed within and are part of the bottoms of the plurality of wells within the microplate.

2. The method of claim 1, wherein each waveguide is isolated from the other waveguides by physically removing at least a portion of a waveguide film which is located around a perimeter of each grating that is formed in the waveguide film.

3. The method of claim 1, wherein each waveguide is isolated from the other waveguides by depositing an absorption material within or upon at least a portion of a waveguide film which is located around a perimeter of each of grating that is formed in the waveguide film.

4. The method of claim 3, wherein said absorption material is a metal film that was vapor-deposited to attenuate propagating light.

5. The method of claim 3, wherein said absorption material is a polymer which contains a light-absorbing dye.

6. The method of claim 1, wherein each waveguide is isolated from the other waveguides by using a mask and an etching/embossing process to pattern disordered structures within at least a portion of a waveguide film which is located around a perimeter of each of grating that is formed within the waveguide film.

7. The method of claim 1, wherein each waveguide is isolated from the other waveguides by using a mask and an etching/embossing process to pattern disordered structures within at least a portion of a substrate where the pattern disordered structures are located around a perimeter of each biosensor grating that is formed within the substrate.

8. The method of claim 1, wherein each waveguide is isolated from the other waveguides by using a mask and depositing individual patches of a waveguide film over a substrate, wherein each patch of waveguide film has one grating formed therein.

9. The method of claim 1, wherein each waveguide is isolated from the other waveguides by using a mask and depositing individual patches of a waveguide film over a substrate, wherein each patch of waveguide film is deposited over a part of the substrate that has one grating formed therein.

10. A microplate comprising:
a frame including a plurality of wells formed therein, wherein each well has a bottom that incorporates a waveguide grating-based biosensor, wherein the plurality of biosensors are formed within and are part of the bottoms of the plurality of wells, wherein each biosensor is isolated from the other biosensors by isolating a waveguide within each biosensor from other waveguides that are within other biosensors to eliminate crosstalk of coupled light between each of the biosensors, wherein the waveguide within each biosensor has coupled light propagating therein, and wherein the plurality of biosensors are formed within and are part of the bottoms of the plurality of wells within the microplate.

11. The microplate of claim 10, wherein each waveguide is isolated from the other waveguides by physically removing at least a portion of a waveguide film which is located around a perimeter of each grating that is formed in the waveguide film.

12. The microplate of claim 10, wherein each waveguide is isolated from other waveguides by depositing an absorption material within or upon at least a portion of a waveguide film located around each of the gratings which are formed in the waveguide film.

13. The microplate of claim 12, wherein said absorption material is a metal film that was vapor-deposited to attenuate propagating light.

14. The microplate of claim 12, wherein said absorption material is a polymer which contains a light-absorbing dye.

15. The microplate of claim 10, wherein each waveguide is isolated from the other waveguides by using a mask and an etching/embossing process to pattern disordered structures within at least a portion of a waveguide film which is located around a perimeter of each grating that is formed within the waveguide film.

16. The microplate of claim 10, wherein each waveguide is isolated from the other waveguides by using a mask and an etching/embossing process to pattern disordered structures within at least a portion of a substrate where the pattern disordered structures are located around a perimeter of each biosensor grating that is formed within the substrate.

17. The microplate of claim 10, wherein each waveguide is isolated from the other waveguides by using a mask and depositing individual patches of a waveguide film over a substrate, wherein each patch of waveguide film has one grating formed therein.

18. The microplate of claim 10, wherein each waveguide is isolated from the other waveguides by using a mask and depositing individual patches of a waveguide film over a substrate, wherein each patch of waveguide film is deposited over a part of the substrate that has one grating formed therein.

19. A slide comprising:
a flat base having a plurality of waveguide grating-based biosensors formed therein, wherein each biosensor is isolated from the other biosensors by isolating a waveguide within each biosensor from other waveguides that are within other biosensors to eliminate crosstalk of coupled light between each of the biosensors, wherein the waveguide within each biosensor has coupled light propagating therein.

20. The slide of claim 19, wherein each waveguide is isolated from the other waveguides by physically removing at least a portion of a waveguide film which is located around a perimeter of each grating that is formed in the waveguide film.

21. The slide of claim 19, wherein each waveguide is isolated from other waveguides by depositing an absorption material within or upon at least a portion of a waveguide film located around each of the gratings which are formed in the waveguide film.

22. The slide of claim 19, wherein each waveguide is isolated from the other waveguides by using a mask and an etching/embossing process to pattern disordered structures within at least a portion of a waveguide film which is located around a perimeter of each grating that is formed within the waveguide film.

23. The slide of claim 19, wherein each waveguide is isolated from the other waveguides by using a mask and an etching/embossing process to pattern disordered structures within at least a portion of the flat base where the pattern disordered structures are located around a perimeter of each biosensor grating that is formed within the flat base.

24. The slide of claim 19, wherein each waveguide is isolated from the other waveguides by using a mask and depositing individual patches of a waveguide film over a substrate, wherein each patch of waveguide film has one grating formed therein.

25. The slide of claim 19, wherein each waveguide is isolated from the other waveguides by using a mask and depositing individual patches of a waveguide film over a substrate, wherein each patch of waveguide film is deposited over a part of the substrate that has one grating formed therein.

26. The method of claim 1, wherein each waveguide grating-based biosensor is an evanescent-wave sensor based on resonant coupling of light into the waveguide by a diffraction grating.

27. The method of claim 1, wherein each waveguide grating-based biosensor includes:
a waveguide film;
a substrate made of a material having a refractive index that is lower than a refractive index of the waveguide film, where the waveguide film is located on top of the substrate, and where the waveguide film has a diffraction grating formed therein.

28. The microplate of claim 10, wherein each waveguide grating-based biosensor is an evanescent-wave sensor based on resonant coupling of light into the waveguide by a diffraction grating.

29. The microplate of claim 10, wherein each waveguide grating-based biosensor includes:
a waveguide film;
a substrate made of a material having a refractive index that is lower than a refractive index of the waveguide film, where the waveguide film is located on top of the substrate, and where the waveguide film has a diffraction grating formed therein.

30. The slide of claim 19, wherein each waveguide grating-based biosensor is an evanescent-wave sensor based on resonant coupling of light into the waveguide by a diffraction grating.

31. The slide of claim 19, wherein each waveguide grating-based biosensor includes:
   a waveguide film;
   a substrate made of a material having a refractive index that is lower than a refractive index of the waveguide film, where the waveguide film is located on top of the substrate, and where the waveguide film has a diffraction grating formed therein.

* * * * *